US005950635A

United States Patent [19]

Garcia-Rill et al.

[11] Patent Number: 5,950,635

[45] Date of Patent: Sep. 14, 1999

[54] SURFACE STIMULATION OF SPECIFIC ACUPUNCTURE POINTS TO REDUCE ANXIETY

[75] Inventors: Edgar Garcia-Rill, Roland; Robert D. Skinner; Harris Gellman, both of Little Rock, all of Ark.

[73] Assignee: Board of Trustees of the University of Arkansas, Little Rock, Ark.

[21] Appl. No.: 09/009,515

[22] Filed: Jan. 20, 1998

[51] Int. Cl.[6] .......................... A61B 19/00; A61B 17/34; A61M 21/00

[52] U.S. Cl. ........................... 128/898; 128/907; 600/26; 606/189

[58] Field of Search .................................... 128/898, 907; 600/26; 606/189, 204, 185, 167

[56] References Cited

U.S. PATENT DOCUMENTS

| | | | |
|---|---|---|---|
| 3,908,669 | 9/1975 | Man et al. | 128/422 |
| 4,055,190 | 10/1977 | Tany | 128/422 |
| 4,503,863 | 3/1985 | Katims | 128/741 |
| 4,981,146 | 1/1991 | Bertolucci | 128/802 |
| 5,269,304 | 12/1993 | Matthews | 607/46 |
| 5,417,706 | 5/1995 | Chun | 606/189 |
| 5,676,684 | 10/1997 | Choi | 606/189 |

OTHER PUBLICATIONS

Meeker, Charles A., "Chinese Acupuncture" (3rd Ed. 1979).

*Primary Examiner*—Mickey Yu
*Assistant Examiner*—Dinh X. Nguyen
*Attorney, Agent, or Firm*—J. Charles Dougherty

[57] ABSTRACT

A method of treating various anxiety-related disorders, such as Post-Traumatic Stress Disorder, panic attacks, or general anxiety disorder is disclosed. It has been found that the P1 midlatency auditory evoked potential of such patients undergoes increased amplitude and decreased habituation. Stimulation of three specific acupuncture points LR3, HT3, and PC6) on three different acupuncture meridians has been found to reduce the amplitude of the P1 potential using 20-minute periods of stimulation. Low frequency stimulation (around 5 Hz) was found to be most effective. Repeated periods of stimulation were also found to increase the effect of the treatment.

7 Claims, 4 Drawing Sheets

SURFACE STIMULATION OF SPECIFIC ACUPUNCTURE POINTS TO REDUCE ANXIETY

BACKGROUND OF THE INVENTION

The present invention relates generally to the stimulation of acupuncture points to effect medical treatment. The present invention relates particularly to the stimulation of three acupuncture points to treat anxiety-related disorders.

For more than three thousand years, Chinese physicians have used acupuncture to alleviate pain and treat a myriad of diseases. While the principles underlying the effectiveness of acupuncture as a treatment form are not yet completely understood, it has been well recognized that the stimulation of certain points on the human body has therapeutic effects. Such stimulation may be effected through the insertion of needles, activation of surface electrodes, or other means.

The practice of acupuncture is based on the theory that certain lines running across the human body, referred to as meridians, are each associated with a certain organ. For example, the Lung Meridian (designated "L") runs from the tip of the thumb, along the forearm above the radius, and up to the shoulder. Other meridians include the Liver Meridian ("LR"), Stomach Meridian ("S"), Spleen Meridian ("SP"), Heart Meridian ("HT"), and Pericardium Meridian ("PC"). Along these meridians are certain points that, when stimulated, have certain effects (either therapeutic or deleterious) on the human body. Points along a meridian are designated by the meridian symbol combined with a number for that point; for example, the point on the Lung Meridian that lies just above the joint between the radius and the humerus is designated "L5". The stimulation of each point along a meridian is believed to have an effect different from the stimulation of other points along the same meridian. Thus according to acupuncture theory, the correct location of the proper meridian, and the correct location of the proper point along that meridian, is crucial to effecting a proper treatment. In particular, the traditional acupuncture treatment to relieve anxiety-related disorders requires the insertion of needles at two specific points, LR3 and HT3. A standard reference work identifying the acupuncture meridians and points, and the believed effects of stimulating many of those points, is Charles A. Meeker, *Acupuncture for the Practitioner or Advanced Student* (3d Ed. 1979), which is incorporated by reference herein.

The use of acupuncture or the stimulation of acupuncture points for the general purposes of medical treatment and research has continued to the present day. The following prior art references demonstrate modern developments in this area:

U.S. Pat. No. 3,908,669 issued to Man et al. is of interest for the prior art of devices using acupuncture in medical research and therapy. Man et al. discloses the use of electrically-charged needles rather than electrodes.

U.S. Pat. No. 4,981,146 issued to Bertolucci discloses a nausea control device for mounting onto the human wrist. Electrodes stimulate the pericardium six (or PC6) acupuncture point.

U.S. Pat. No. 5,269,304 issued to Matthews discloses an electro-therapy apparatus including at least two electrodes. Matthews suggests the efficacy of higher frequencies up to around 200 kHz, but also suggests employing slightly different frequencies on the two electrodes so as to achieve beat frequencies of 80 to 130 Hz.

U.S. Pat. No. 4,055,190 issued to Tany discloses an electrical therapeutic apparatus for applying selected voltages and frequencies to various acupuncture meridians through needles. Suggested frequencies for each meridian are disclosed ranging from 500 Hz to 200 kHz.

U.S. Pat. No. 5,417,706 issued to Chun is the most relevant to the present invention. Chun discloses a method of treating various types of baldness by inserting acupuncture needles into selected acupuncture points on multiple meridians. Chun identifies twelve particular acupuncture points on eight different meridians as effective in the therapy.

It is known, therefore, in the prior art to employ surface stimulation over acupuncture points to alleviate various medical conditions. It is also known to employ multiple acupuncture points on multiple meridians to treat various conditions of baldness. It is also known that the stimulation of specific acupuncture points with needles may be used to treat anxiety and related disorders. In particular, the traditional prior art acupuncture treatment for anxiety and related disorders was the insertion of needles at two specific points, LR3 and HT3.

Our studies have shown that, contrary to accepted acupuncture practice, the use of two acupuncture points alone is ineffective in reducing arousal in normal subjects and in treating patients with anxiety-related disorders. It was thus not recognized in the prior art that the effective treatment of Post-Traumatic Stress Disorder and other anxiety-related disorders requires that at least three acupuncture points be stimulated. Nor was it recognized that these three points may lie along three different meridians. Nor was it recognized in the prior art that the three specific points identified in the disclosed invention (HT3, PC6, and LR3) may be used in combination to effectively treat anxiety-related disorders. Nor was it recognized that a low electrode frequency of about 5 Hz is most effective in treating anxiety-related disorders.

SUMMARY OF THE INVENTION

The present invention is a method of treating various anxiety-related disorders, such as Post-Traumatic Stress Disorder, panic attacks, or general anxiety disorder. Patients suffering from such conditions typically experience severe reactions to relatively mild stimuli (for example, auditory stimuli). The present invention treats such conditions by stimulating three different acupuncture points. It has been found that the stimulation of three points on three different meridians, particularly the points LR3, HT3, and PC6, has an arousal-reducing effect on normal subjects and may have a therapeutic effect for sufferers of anxiety-related disorders. This effect is not seen when only the two points LR3 and HT3 are stimulated. The LR3 acupuncture point is roughly located on the top of the foot, 2 cm proximal to the margin of the first and second toes. The HT3 acupuncture point is roughly located on the inside of the elbow, midway between the medial end of the elbow crease and the medial epicondyle of the humerus when the elbow is fully flexed. The PC6 acupuncture point is roughly located on the wrist, 2 cm proximal to the midpoint of the wrist crease, between the tendons of the palmaris longus and the flexor carpi radialis muscles.

Although treatment may be effected using acupuncture needles charged with an electrical current, surface electrodes may also be used. Both types of stimulus devices are well known in the prior art. Low frequency stimuli have been found most effective, operating at a frequency of about 5 Hz.

In patients with anxiety-related disorders, the P1 midlatency auditory evoked potential undergoes increased amplitude and decreased habituation. The P1 potential is a positive wave recorded at the scalp occurring at a 40–70 msec latency following auditory stimulation of the patient. This potential is a measure of reticular activating system output, that is, cortical desynchronization or arousal. The P1 potential is present during waking and REM sleep, but absent during drowsiness and slow wave sleep. The P1 potential is believed to have at least one subcortical source, specifically in the pedunculopontine nucleus (PPN), the cholinergic arm of the reticular activating system.

The P1 potential is exaggerated in disorders which are characterized by hyperarousal, such as schizophrenia and anxiety disorder, and is absent or reduced in disorders characterized by hypoarousal, such as narcolepsy. Thus the amplitude of a patient's P1 potential following auditory stimulation may be measured as an indicator of the severity of the patient's anxiety-related disorder. A reduction in amplitude of the subject's P1 potential indicates a reduction in arousal in normal subjects and consequently indicates a reduction of anxiety in anxiety-disorder patients. Further information concerning the source of the P1 potential and its relationship to arousal level is found at N. B. Reese et al., *The Pedunculopontine Nucleus-Auditory Input, Arousal, and Pathophysiology*, Elsevier, Amsterdam 461–67 (1987), which is incorporated by reference herein.

It has been found that the use of acupuncture needles or surface electrodes at the LR3, HT3, and PC6 points causes a statistically significant reduction in a subject's P1 potential. Thus stimulation at these three points is demonstrated to have a potentially therapeutic effect on patients suffering from anxiety-related disorders. A rebound effect immediately after cessation of the stimulation causes the amplitude of the P1 potential to rise initially but then taper off to an amplitude lower than that reached before stimulation was applied. It has further been found that electrodes or needles using low frequency stimuli, in the range of about 5 Hz, result in the greatest reduction in P1 potential amplitude. It has also been found that repeated treatments using low-frequency stimuli at the identified points results in a greater reduction in the P1 potential amplitude than single treatments standing alone.

The novelty of the present invention therefore resides in the recognition that effective reduction of the P1 potential may represent effective treatment of Post-Traumatic Stress Disorder and related disorders, and requires that at least three acupuncture points be stimulated. It is also significant that the three points are on three different meridians, and that the specific points identified (LR3, HT3, and PC6) have not in combination been identified as having this effect. It is further novel to use low frequency stimuli at about 5 Hz to achieve this therapeutic effect. In addition, it is novel that repeated treatments yield superior results over a single treatment standing alone.

It is therefore an object of the present invention to provide for the treatment of anxiety-related disorders by stimulating three different acupuncture points.

It is also an object of the present invention to provide for the treatment of anxiety-related disorders by stimulating acupuncture points on three different meridians.

It is a further object of the present invention to provide for the treatment of anxiety-related disorders by the placement of needles or surface electrodes at the LR3, HT3, and PC6 acupuncture points in combination.

It is an additional object of the present invention to provide for the treatment of anxiety-related disorders using needles or electrodes passing a relatively low-frequency current of about 5 Hz.

It is a still further object of the present invention to provide for the treatment of anxiety-related disorders using multiple treatments of needles or surface electrodes.

These and other objects and advantages of the present invention will be apparent from a consideration of the following detailed description of the preferred embodiments in conjunction with the drawings which are briefly described as follows:

DETAILED DESCRIPTION OF THE PREFERRED EMBODIMENTS

Figure 1:
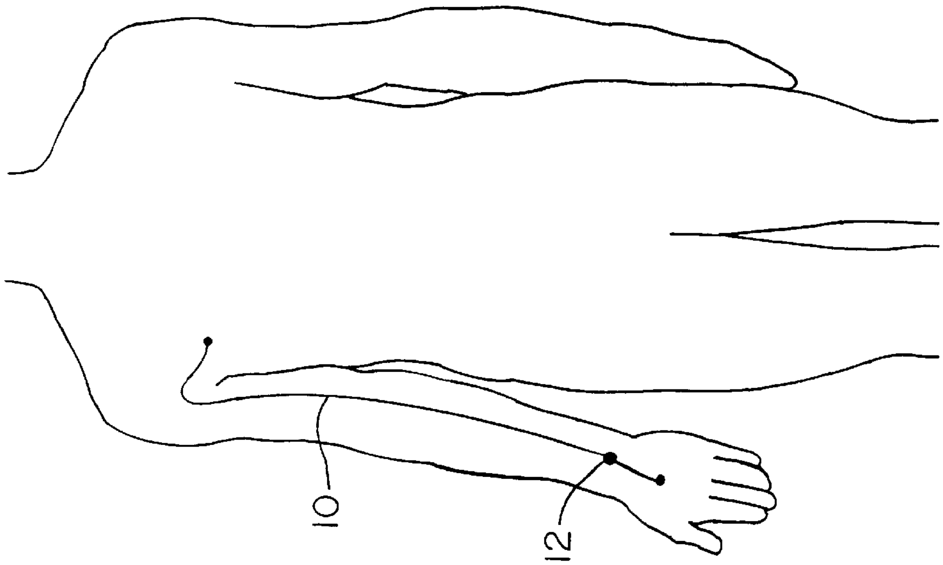
FIG. 1 is a partial front view of the human body showing the Pericardium Meridian and the location of the PC6 acupuncture point.
Figure 2:
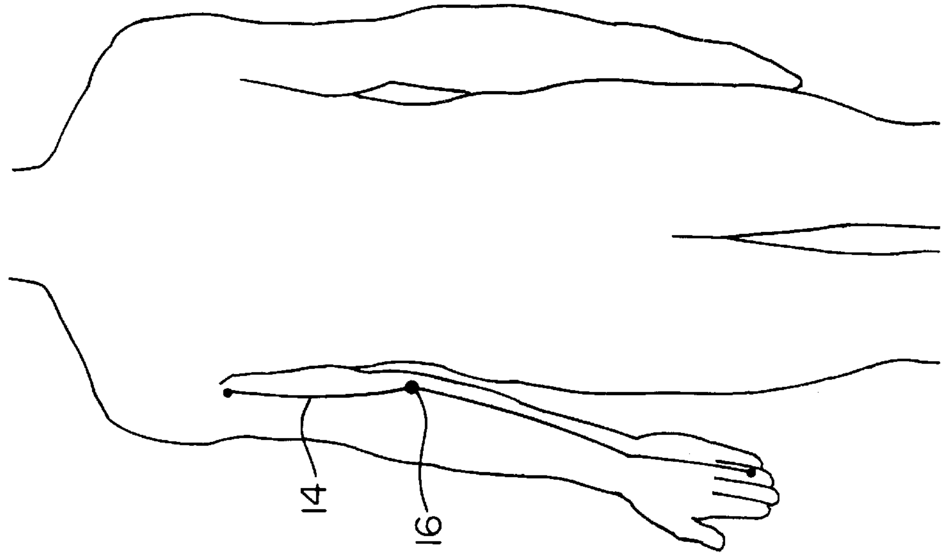
FIG. 2 is a partial front view of the human body showing the Heart Meridian and the location of the HT3 acupuncture point.
Figure 3:
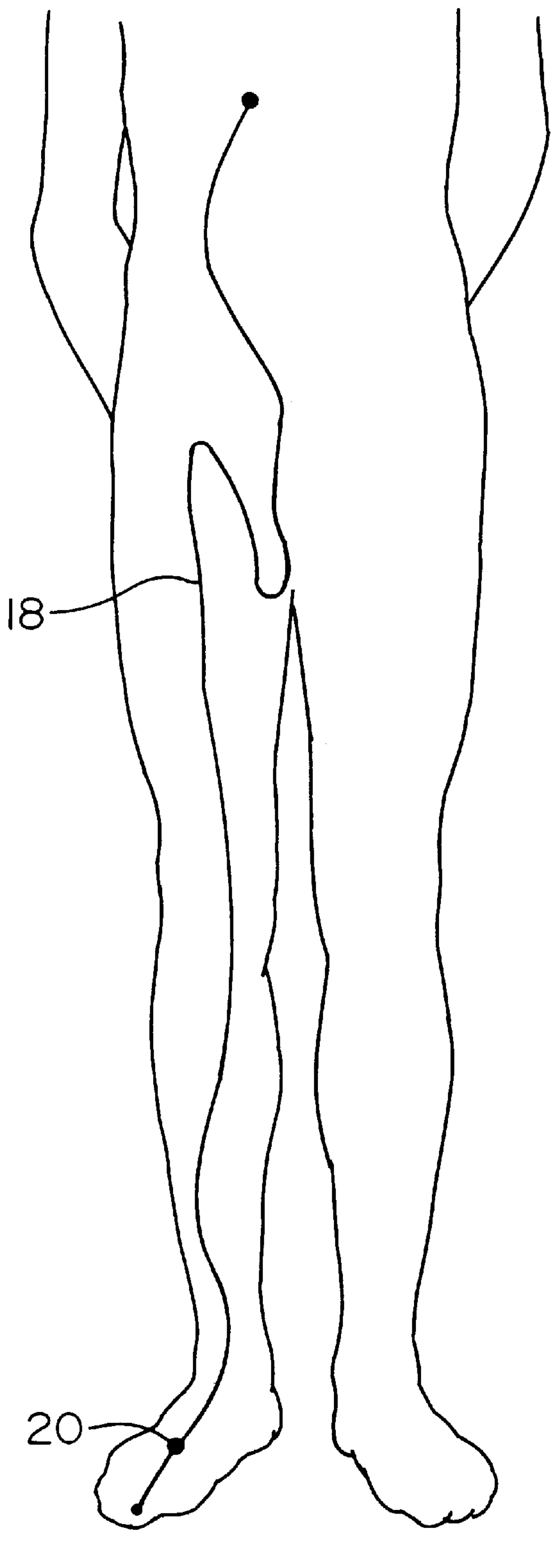
FIG. 3 is a partial front view of the human body showing the Liver Meridian and the location of the LR3 acupuncture point.

The preferred embodiment of the present invention may be described with reference to FIGS. 1–3. FIG. 1 shows the location of the Pericardium Meridian 10. The acupuncture point PC6 is shown at 12. FIG. 2 shows the location of the Heart Meridian 14. The acupuncture point HT3 is shown at 16. FIG. 3 shows the location of the Liver Meridian 18. The acupuncture point LR3 is shown at 20. Acupuncture point PC6, shown at 12, acupuncture point HT3, shown at 16, and acupuncture point LR3, shown at 20, are stimulated with needles or surface electrodes while using the present invention as described below.

To measure the effects of stimulating the LR3, HT3, and PC6 points and thereby confirm the results of the present invention, recordings of the P1 potential were made of subjects sitting on a recliner with eyes open. The P1 potential was recorded in a standard fashion at the scalp from a vertex electrode referred to a frontal electrode, with correction for eye and muscle artifacts. Stimulation was delivered through earphones at a rate of 0.2 Hz using rarefied click stimuli at 50 dB above hearing threshold. Separate tests were conducted using needles and surface electrodes.

Electrical current was applied to the needles or surface electrodes using a TENS stimulator. The amplitude of the current was set by raising the amplitude until the patient experienced a detectable tingling sensation. The current was then applied in 20-minute treatment periods. It was discovered that the decrease in P1 potential amplitude was greatest when the frequency applied was about 5 Hz. A greater decrease in P1 potential amplitude was also observed when multiple 20-minute stimulation periods were used.

Figure 4:
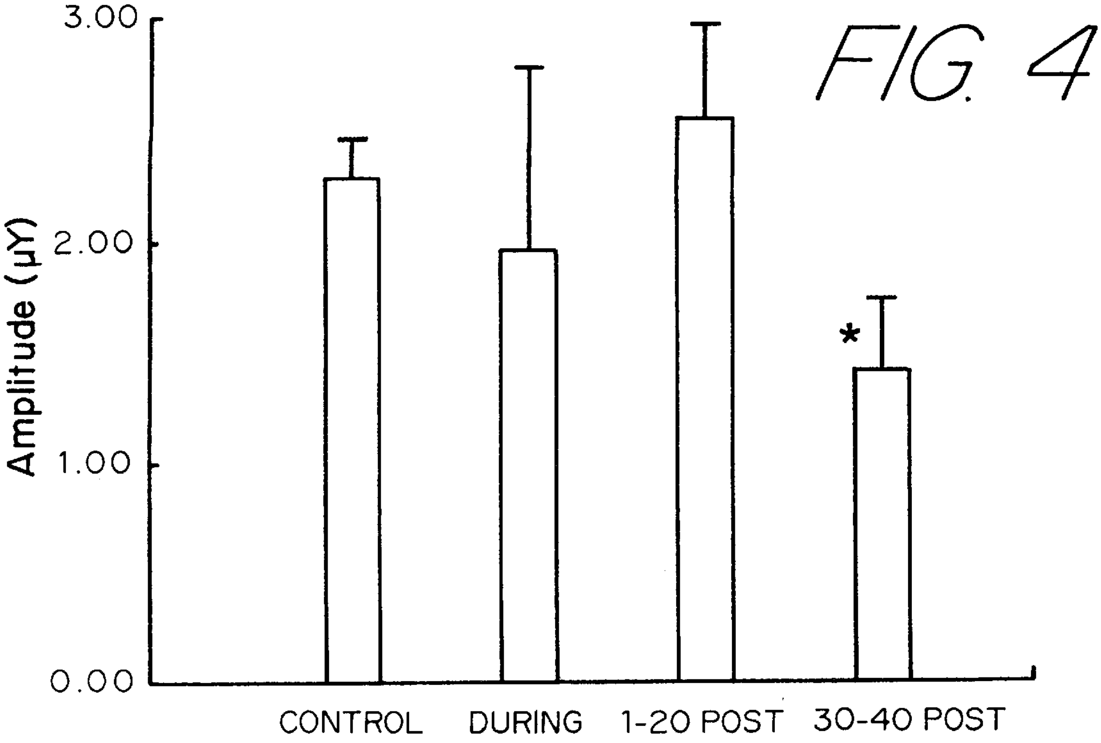
FIG. 4 is a bar graph illustrating the results of a first series of experiments using needles to stimulate the acupuncture points.
Figure 5:
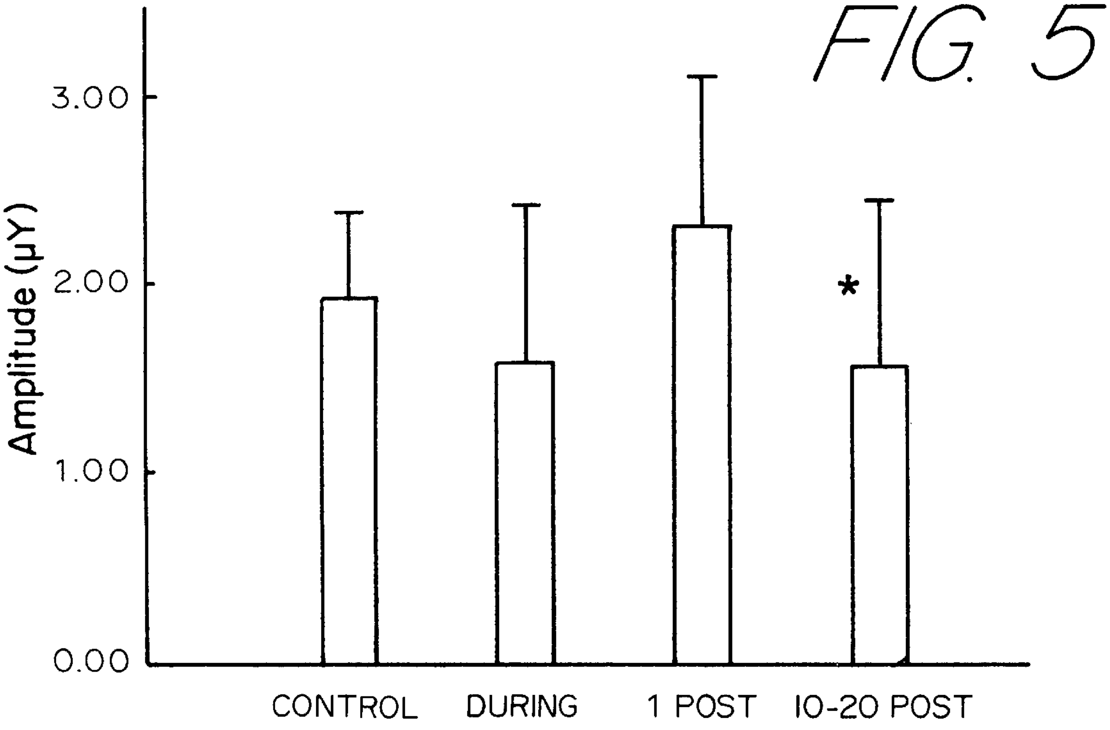
FIG. 5 is a bar graph illustrating the results of a first series of experiments using surface electrodes to stimulate the acupuncture points.

In a first series of experiments, the subjects were exposed to conditions as described above using needles or surface electrodes and a current oscillating at 100 Hz. Only one 20-minute period of stimulation was applied during these experiments. The results of the experiments using needles are shown by the graph of FIG. 4, and the results of the experiments using surface electrodes are shown by the graph of FIG. 5. Both graphs depict the average amplitude of the Pi potential as measured during key sections of the experiment: control, which represents the P1 potential of the subjects before any stimulation took place, the P1 potential during the stimulation, the P1 potential during the period from 1–20 minutes after the cessation of stimulation, and the P1 potential during the period 30–40 minutes after the cessation of stimulation. Four subjects were used in each of these experiments.

The data from this first series of experiments demonstrates a statistically significant drop in P1 potential amplitude from that measured during the period 1–20 minutes after the cessation of stimulation to that measured during the period 30–40 minutes after the cessation of stimulation. A statistically significant drop resulted whether needles or surface electrodes were used. In particular, the p-value for these data points was 0.0001 when needles were used and 0.004 when surface electrodes were used. P-values are a commonly used statistical indicator ranging from 0 to 1 and indicating the probability that random sampling would lead to a difference between sample means as large or larger than were actually observed. Thus the chance that the difference evidenced by the first series of experiments was simply the result of random sampling is less than one percent. The change in P1 amplitude value between the control period before the stimulation was begun and the 30–40 minute period after stimulation ended was found to not be statistically significant.

Figure 6:
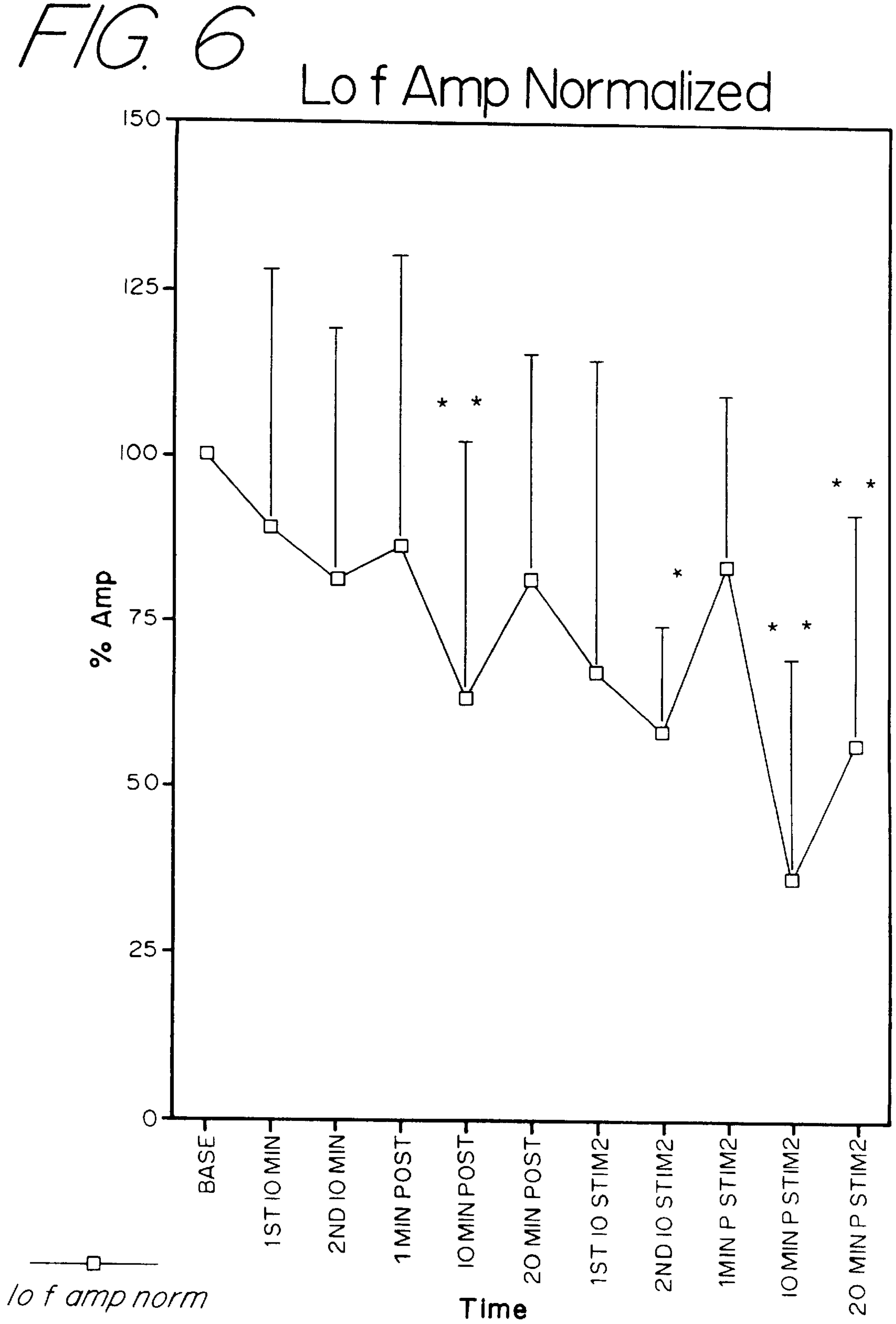
FIG. 6 is a plot graph illustrating the results of a second series of experiments using surface electrodes to stimulate the acupuncture points.

In a second series of experiments, multiple stimulation periods were applied to test subjects using a low-frequency current of about 5 Hz. The normalized results of these experiments are shown in FIG. 6 as a function of a percentage increase or decrease in amplitude of the subject's P1 potential compared to that measured before surface stimulation was begun. Data points plotted in FIG. 6 illustrate the relative P1 amplitude after the first 10 minutes of stimulation, after the second 10 minutes of stimulation, 1 minute after the first stimulation period ended, 10 minutes after the first stimulation period ended, twenty minutes after the first stimulation period ended, after the first 10 minutes of the second stimulation period, after the second 10 minutes of the second stimulation period, 1 minute after the second stimulation period ended, 10 minutes after the first stimulation period ended, and twenty minutes after the first stimulation period ended. For these experiments, 8 subjects were exposed to only the first stimulation period and 4 subjects were exposed to both the first and second stimulation periods.

Statistically significant decreases in relative P1 amplitude were observed between the base amplitude and those amplitudes measured 10 minutes after the first stimulation period began, 20 minutes after the first stimulation period began, 10 minutes after the second stimulation period began, and 20 minutes after the second stimulation period began. P-values for those differences were less than 0.01, 0.05, 0.01, and 0.01, respectively. Thus the use of the lower-frequency current yielded an improved reduction in P1 amplitude, as did the application of the stimulation for multiple periods.

The present invention has been described with reference to certain preferred and alternative embodiments which are intended to be exemplary only and not limiting to the full scope of the present invention as set forth in the appended claims.

What is claimed is:

1. A method for the treatment of anxiety-related disorders, comprising the steps of:

(a) engaging an electrode with each of acupuncture points LR3 HT3, and PC6 on a subject; and (b) applying an electrical current to said electrodes.

2. The method of claim 1, wherein said electrical current oscillates at a frequency of about 5 Hz.

3. The method of claim 1, wherein said electrical current is applied for about twenty minutes.

4. The method of claim 1, wherein step (b) is performed using a plurality of applications of said electrical current interspaced by a plurality of periods during which said electrical current is not applied.

5. The method of claim 4, wherein each of said applications of said electrical current is about 20 minutes in duration.

6. The method of claim 1, wherein said electrodes are acupuncture needles, and said acupuncture needles are engaged with said acupuncture points by inserting said acupuncture needles into the subject at said acupuncture points.

7. The method of claim 1, wherein said electrodes are surface electrodes, and said surface electrodes are engaged with said acupuncture points by placing said surface electrodes onto the patient at said acupuncture points.

* * * * *